(12) United States Patent
Orlandi et al.

(10) Patent No.: US 7,315,787 B2
(45) Date of Patent: Jan. 1, 2008

(54) MULTI-MARKER SCREENING PROTOCOL FOR FETAL ABNORMALITIES

(75) Inventors: Francesco Orlandi, Palermo (IT); David Krantz, Bayside, NY (US)

(73) Assignee: NTD Laboratories, Inc., Huntington Station, NY (US)

( * ) Notice: Subject to any disclaimer, the term of this patent is extended or adjusted under 35 U.S.C. 154(b) by 0 days.

(21) Appl. No.: 10/679,258

(22) Filed: Oct. 7, 2003

(65) Prior Publication Data

US 2005/0074783 A1    Apr. 7, 2005

(51) Int. Cl.
  *G06F 19/00*    (2006.01)
  *G06F 7/06*     (2006.01)
  *A61N 7/00*     (2006.01)
  *G06K 9/20*     (2006.01)

(52) U.S. Cl. .......................... 702/19; 702/22; 702/181; 382/128; 382/282; 382/286; 128/916; 424/9.1

(58) Field of Classification Search ................ 702/19, 702/22, 181, 155; 382/282, 286, 128; 128/916
  See application file for complete search history.

(56) References Cited

U.S. PATENT DOCUMENTS

| | | |
|---|---|---|
| 5,100,806 A | 3/1992 | Macri |
| 5,252,489 A | 10/1993 | Macri |
| 5,258,907 A | 11/1993 | Macri |
| 5,316,953 A | 5/1994 | Macri |
| 5,324,667 A | 6/1994 | Macri |
| 5,324,668 A | 6/1994 | Macri |
| 5,605,843 A | 2/1997 | Canick et al. |
| 5,716,853 A | 2/1998 | Cuckle et al. |
| 5,772,584 A * | 6/1998 | Davies ............... 600/300 |
| 5,834,317 A | 11/1998 | Davies |
| 5,840,586 A | 11/1998 | Davies |
| 5,906,944 A | 5/1999 | Davies |
| 6,010,912 A | 1/2000 | Davies |
| 6,022,695 A | 2/2000 | Beard et al. |
| 6,025,149 A | 2/2000 | Cuckle et al. |
| 6,429,018 B1 | 8/2002 | Cole et al. |
| 6,573,103 B1 * | 6/2003 | Wald .................... 436/65 |

OTHER PUBLICATIONS

Bromley et al. (Journal of Ultrasound in Medicine (2000) vol. 21, pp. 1087-1096).*
Stempfle et al. (Pediatric Radiology (1999) vol. 29, pp. 682-688).*
Merkatz IR, et al., "An association between low maternal serum alpha-fetoprotein and fetal chromosomal abnormalities," Am. J. Obstet. Gynecol., 148:886-894 (1984).
Stempfle N., et al., "Skeletal abnormalities in fetuses with Down's syndrome: a radiographic post-mortem study," Pediatr. radiol., 29:682-688 (1999).
Lockwood C., et al., "A sonographic screening method for Down syndrome," Am. J. Obstet. Gynecol., 157:803-808 (1987).
Buttery B., "Occipitofrontal-Biparietal Diameter Ratio. An Ultrasonic Parameter for the Antenatal Evaluation of Down's Syndrome," Med. J. Aust., 2:662-664 (1979).
Borrel A., et al., "Brachycephaly is ineffective for detection of Down syndrome in early midtrimester fetuses," Early Human Dev., 47:57-61 (1997).
Rosati P. et al., "Early Transvaginal Measurement of Cephalic Index for the Detection of Down Syndrome Fetuses," Fetal Diagn. and Therapy, 14:38-40 (1999).
Platt L.D., et al., "Screening for Down syndrome with the femur length/biparietal diameter ratio: A new twist of the data," Am. J. Obstet. Gynecol., 167:124-128 (1992).
PCT/US04/31928 Notification of Transmittal of The International Search Report dated Apr. 25, 2005.

* cited by examiner

*Primary Examiner*—Lori A. Clow
(74) *Attorney, Agent, or Firm*—Daniel P. Burke & Associates, PLLC

(57) ABSTRACT

A method of assessing a pregnant woman's risk of having a fetus with a fetal abnormality by determining the fetus' BPD/OFD ratio and using the BPD/OFD ratio in conjunction with one or more other screening markers for the fetal abnormality. Also provided is a method of determining whether a pregnant woman is screen-positive or screen-negative by comparing the BPD/OFD ratio of the pregnant woman's fetus to a risk cut-off level.

38 Claims, 3 Drawing Sheets

MULTI-MARKER SCREENING PROTOCOL FOR FETAL ABNORMALITIES

FIELD OF THE INVENTION

The present invention relates to a method of assessing a pregnant woman's risk of having a fetus with a fetal abnormality, such as Down Syndrome, by using the ratio of the fetus' bi-parietal diameter and occipito-frontal diameter in combination with other maternal or fetal screening marker (s) for the fetal abnormality.

BACKGROUND OF THE INVENTION

Trisomy 21, commonly referred to as Down Syndrome, is the most frequent fetal chromosomal abnormality, affecting approximately 1 in 800 infants. It is associated with mental retardation, structural defects involving the heart and/or the digestive tract, increased incidence of respiratory infections, high incidence of fluctuating hearing loss, and thryoid and cervical spine abnormalities.

Generally, Down Syndrome can only be diagnosed by invasive procedures such as amniocentesis, which involves sampling the amniotic fluid, and chorionic villus sampling (CVS), which involves sampling the chorionic villi from the placenta. These invasive diagnostic procedures, however, involve risk to the mother and the fetus and therefore are not routinely performed during all pregnancies. Instead, one or more screening methods may be utilized to determine whether the risk of Down Syndrome to the pregnancy warrants the risk of undergoing an invasive and risky diagnostic procedure. Such Down Syndrome screening methods typically include measuring levels of screening markers such as free β human gonadotrophin (hCG), pregnancy associated during the first trimester of pregnancy. Although screening methods using such markers can detect 85-90% of Down Syndrome cases, they do so at a 5% false positive rate.

Currently research, therefore, is now focused on modifying the 85-90% screening protocol to lower the 5% false positive rate while maintaining the 85-90% detection efficiency. For example, one approach described in Wald N J, Watt H C, Hackshaw, A K. *N. Engl J Med,* 341(7):461-7 (Aug. 12, 1999) suggests measuring levels of screening markers during two stages of pregnancy, i.e. during the first and second trimester to determine a patient's risk of having a fetus with Down Syndrome. Although such an approach may reduce the false positive rates of detection, it presents the disadvantage of not providing a result until later in pregnancy. A better approach would be using additional screening markers during the first trimester to maintain the advantages of early detection. Two additional markers that have been suggested are blood flow in the ductus venous and nasal bone identification. Measurement of both of these markers, however, is quite difficult to perform and requires a significant amount of training even for experienced sonographers. In addition, there is some concern about the safety of using color Doppler ultrasound during pregnancy to measure the ductus venosus blood flow.

Accordingly, there is a need for additional methods of screening for fetal abnormalities, such as Down Syndrome, that carry a low false positive rate and that can easily and safely be performed early in pregnancy.

SUMMARY OF THE INVENTION

The present invention provides a method of assessing a pregnant woman's risk of having a fetus with a fetal abnormality by using a specific ultrasound marker in a multiple-marker screening protocol. In particular, the method of the present invention involves determining the BPD/OFD ratio of the fetus from an ultrasound or other imaging scan. This BPD/OFD ratio marker is then used in conjunction with one or more other screening markers for the fetal abnormality to assess the pregnant woman's risk of having a fetus with the fetal abnormality.

Specifically, the present invention provides a method of assessing a patient's ratio of the patient's fetus and determining at least one secondary marker measurement corresponding to the patient. The BPD/OFD ratio of the patient's fetus and the at least one secondary marker measurement corresponding to the patient is then compared with observed relative frequency distributions of fetal BPD/OFD ratios and at least one secondary marker measurements from observed affected and observed unaffected pregnancies. A result of this comparison is used with the patient's a priori risk to assess the patient's risk of having the fetus with the fetal abnormality.

The present invention also provides a method of determining whether a patient is screen-positive or screen-negative for having a fetus with a fetal abnormality by selecting a risk cut-off level. The method includes determining a BPD/OFD ratio of the patient's fetus and determining at least one secondary marker measurement corresponding to the patient. The method further includes calculating a likelihood ratio for the patient based on the BPD/OFD ratio of the patient's fetus and the at least one secondary marker measurement corresponding to the patient. The method then includes multiplying the patient's likelihood ratio by the patient's a priori risk to determine the patient's risk for a fetal abnormality. The method moreover includes determining whether the patient is screen-positive or screen-negative by comparing the patient's risk to the risk-cut off level. If the patient's risk is greater than or equal to the risk-cut off level, then the patient is screen-positive, and if the patient's risk is less than the risk cut-off level, then the patient is screen-negative.

The present invention also provides a machine-readable medium having stored thereon a plurality of executable instructions, the plurality of executable instructions comprising receiving or calculating a BPD/OFD ratio of a patient's fetus and receiving at least one secondary marker measurement corresponding to the patient. The plurality of executable instructions further comprises performing a comparison of the BPD/OFD ratio of the patient's fetus and the at least one secondary marker measurement corresponding to the patient with observed relative frequency distributions of fetal BPD/OFD ratios and at least one secondary marker measurements from observed affected and observed unaffected pregnancies. The plurality of executable instructions further includes assessing the patient's risk of having a fetus with a fetal abnormality in view of a result of the comparison and the patient's a priori risk of having a fetus with the fetal abnormality.

BRIEF DESCRIPTION OF THE DRAWINGS

The present invention will become more fully understood from the detailed description given herein below and the accompanying drawings which are given by way of illustration only and wherein.

DETAILED DESCRIPTION OF THE INVENTION

In general, the present invention provides a method of assessing a patient's risk of having a fetus with a fetal abnormality by using the bi-parietal diameter to occipito-frontal diameter (BPD/OFD) ratio of the patient's fetus as a primary screening marker in a multiple-marker screening protocol. In the context of the present invention, the patient is a pregnant woman carrying a fetus who is being screened for a fetal abnormality. In particular, the present invention provides a method of assessing a patient's risk of having a fetus with a fetal abnormality by determining a BPD/OFD ratio of the patient's fetus and determining at least one secondary marker measurement corresponding to the patient. The BPD/OFD ratio of the patient's fetus and the at least one secondary marker measurement corresponding to the patient is then compared with relative frequency distributions of fetal BPD/OFD ratios and at least one secondary marker measurements from observed affected and observed unaffected pregnancies. The result of this comparison is then used with the patient's a priori risk to assess the patient's risk of the fetal abnormality.

Figure 1:
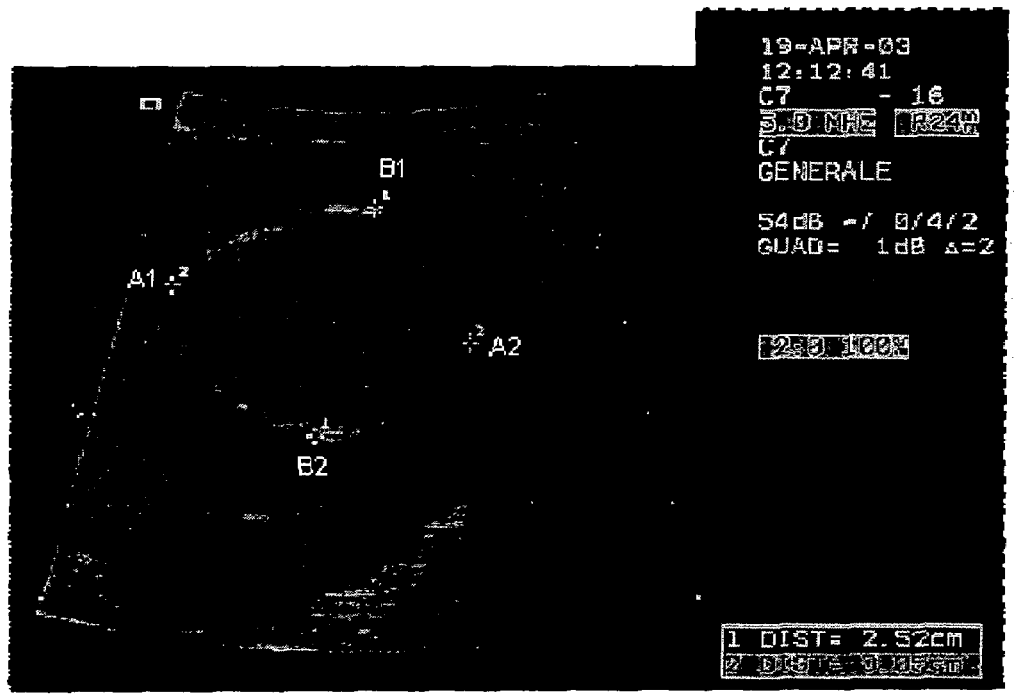
FIG. 1 is an exemplary ultrasound image of a top view of a fetus' head depicting the occipital-frontal diameter (the distance between A1 and A2) and the bi-parietal diameter (the distance between B1 and B2) of the fetus.

With respect to the first step of the method of the present invention, determining the BPD/OFD ratio of the patient's fetus involves measuring or obtaining measurements of the OFD and the BPD of the patient's fetus. Measuring the OFD and BPD of the fetus can be done according to any technique known to one of skill in the art so long as the measurement technique is used consistently with the patient's fetus and the fetuses of the observed affected and the observed unaffected pregnancies. For example, referring to FIG. 1, which is an exemplary ultrasound image of a top view of a fetus' head, the OFD (the distance between A1 and A2) can be measured from the outer-to-outer edges of the occipital bone and frontal bone, the inner-to-inner edges of the occipital bone and the frontal bone, or the inner edge of one of the frontal and occipital bones to the outer edge of the other one of the frontal and occipital bones. The BPD (the distance between B1 and B2) can be measured, for example, from the most distant opposite points of the two parietal bones. Preferably, such measurements are taken during the first trimester of pregnancy. The BPD/OFD ratio of the patient's fetus can then be calculated by dividing the BPD (B1-B2) by the OFD (A1-A2). Although the present invention will be described in terms of the BPD/OFD ratio, use of the inverse of this ratio (i.e. the OFD/BPD ratio) or any other mathematical combination of the OFD and BPD values to determine a patient's risk of a fetal abnormality is also contemplated by the present invention.

With respect to the second step of the method of the present invention, determining at least one secondary marker measurement corresponding to the patient involves measuring or obtaining measurements of any additional screening marker for the fetal abnormality from the patient or her fetus. Although determining a secondary marker measurement is referred to as the second step of the method of the present invention, such a measurement can be done before, after, or concurrently with determining the BPD/OFD ratio of the patient's fetus. Such secondary markers may be, for example, markers detected or measured by ultrasound or other imaging techniques of the fetus or biochemical markers detected from a bodily fluid sample obtained from the patient. The precise identity of such markers depends, of course, on the fetal abnormality for which the patient is being screened. Such fetal abnormalities for which the patient can be screened are any fetal abnormalities where the BPD/OFD ratio can serve as a marker and abnormalities and chromosomal abnormalities. Furthermore, which secondary marker measurements are taken will depend on the identity of the abnormality for which the patient is being screened. Table I summarizes secondary markers that can be measured, as well as which trimester these measurements can be taken, for exemplary fetal abnormalities for which a patient can be screened according to the present invention.

TABLE I

| Marker | Type | Trimester | Fetal Abnormality |
| --- | --- | --- | --- |
| Total Human Chorionic Gonadotropin (hCG) | Biochemical | Second | T21, T18 |
| Alpha Fetoprotein | Biochemical | Second | T21, T18, OSB |
| Unconjugated Estriol | Biochemical | Second | T21, T18 |
| Total Estriol | Biochemical | First and Second | T21, T18 |
| Pregnancy Associated Placental Protein A (PAPP-A) | Biochemical | First | T21, T18, T13, Triploidy |
| Pregnancy Associated Placental Protein A (PAPP-A) | Biochemical | Second | T18 |
| Inhibin A | Biochemical | Second | T21 |
| Free Beta hCG | Biochemical | First and Second | T21, T18, Turner Syndrome, Triploidy |
| Free Beta hCG | Biochemical | First | T13 |
| Free Alpha hCG | Biochemical | Second | T21 |
| Hyperglycosylated hCG | Biochemical | Second | T21 |
| Nuchal Translucency | Ultrasound | First | T21, T18, Turner Syndrome |
| Nuchal Fold Thickness | Ultrasound | Second | T21 |
| Femur Length | Ultrasound | Second | T21 |
| Humerus Length | Ultrasound | Second | T21 |
| Hyperechogenic Bowel | Ultrasound | Second | T21 |
| Renal Pyelectasis | Ultrasound | Second | T21 |
| Fetal Heart Rate | Ultrasound | First | T21, T13, Turner Syndrome |
| Echogenic Foci | Ultrasound | Second | T21 |
| Ductus Venosus Blood Flow | Ultrasound | First or Second | T21 |
| Absent or Hypoplastic Nasal Bone | Ultrasound | First or Second | T21, T18, T13 |
| Intra-Uterine Growth Retardation (IUGR) | Ultrasound | First | T18, T13 |
| Exomphalos | Ultrasound | First | T18, T13 |
| Micrognathia | Ultrasound | First | T18, T13 |

T21 = Trisomy 21
T13 = Trisomy 13
T18 = Trisomy 18
OSB = Open Spina Bifida

The first trimester, as referred to in Table I, is usually less than 14 weeks gestation, although some studies of first trimester markers include cases at 14 weeks gestation. The second trimester, as referred to in Table I, indicates 14 weeks to 22 weeks gestation although some studies of second trimester markers may include cases beyond 22 weeks gestation.

With respect to the biochemical markers that can be used according to the present invention, such markers can be obtained from any bodily fluid of the pregnant woman including the blood, urine, saliva, or amniotic fluid and the levels of such biochemical markers can be measured by any conventional analytical method known in the art. Such conventional analytical methods include, for example, radioimmunoassay, ELISA, chemiluminescence immunoassay, fluorescence immunoassay, in situ hybridization, gel electrophoresis, and spectrophotometric methods.

Any combination of secondary markers for the respective fetal abnormalities can be used and the present invention contemplates any number of secondary markers (and not just a single secondary marker) used in conjunction with the BPD/OFD ratio marker to assess the patient's risk of a fetal abnormality. In fact, to increase the fetal abnormality detection efficiency, in a preferred embodiment, a plurality of secondary marker measurements corresponding to the patient are obtained and compared to the observed relative frequency distributions of each of the plurality of secondary marker measurements in both the observed affected and the observed unaffected pregnancies.

The third step of the method of the present invention comprises performing a comparison of the BPD/OFD ratio of the patient's fetus and the at least one secondary marker measurement corresponding to the patient with observed relative frequency distributions of fetal BPD/OFD ratios and at least one secondary marker measurements from observed affected and observed unaffected pregnancies. By "observed affected pregnancies" is meant observed pregnancies from reference data of pregnant women carrying fetuses with the fetal abnormality for which the patient is being screened. By "observed unaffected pregnancies" is meant observed pregnancies from reference data of pregnant women carrying fetuses that do not have the fetal abnormality for which the patient is being screened.

Such a comparison according to the third step of the method of the present invention may be performed by calculating a likelihood ratio, which is the quotient of the relative frequency of the affected distribution divided by the relative frequency of the unaffected distribution. The relative frequency of the affected distribution is determined by comparing the BPD/OFD ratio of the patient's fetus and the at least one secondary marker measurement corresponding to the patient to fetal BPD/OFD ratios and at least one secondary marker measurements from the observed affected pregnancies. The relative frequency of the unaffected distribution is determined by comparing the BPD/OFD ratio of the patient's fetus and the at least one secondary marker measurement corresponding to the patient to fetal BPD/OFD ratios and at least one secondary marker measurements from the observed unaffected pregnancies. The relative frequencies of each of the unaffected distribution and the affected distribution can be specifically calculated by many different ways which are all well-known in the art. For example, in one implementation of this step of the method of the present invention, the relative frequencies are determined by grouping the observed pregnancies from each of the affected and unaffected pregnancies into pre-determined categories of BPD/OFD ratios and secondary marker measurements. In another implementation, the relative frequencies are determined by using known statistical distributions.

With respect to the predetermined categories implementation, each of the observed pregnancies are categorized into pre-determined categories of BPD/OFD ratios based on the BPD/OFD ratio of the fetus from each of the observed pregnancies. Similarly, each of the observed pregnancies are categorized into pre-determined categories of secondary marker measurements based on the at least one secondary marker measurement from each of the observed pregnancies. The percentage of observed affected and observed unaffected pregnancies that belong to each of the pre-determined categories is determined. The pre-determined categories in which the observed pregnancies are categorized can be quantitative or qualitative ranges of marker values, such as ranges of marker levels, determined by the clinician, empirical evidence, or random categorization. Likelihood ratios are derived for each of the pre-determined categories of BPD/OFD ratios by dividing the percentage of observed affected pregnancies in each of the pre-determined categories by the percentage of observed unaffected pregnancies in each of the pre-determined categories of BPD/OFD ratios. The patient who is being screened is then assigned one of the likelihood ratios based on the pre-determined category that corresponds to the BPD/OFD ratio of the patient's fetus (i.e. the pre-determined category under which the BPD/OFD ratio of the patient's fetus falls.) Likelihood ratios can also be derived for each of the pre-determined categories of secondary marker measurements by dividing the percentage of observed affected pregnancies by the percentage of observed unaffected pregnancies in each of the pre-determined categories of secondary marker measurements. The patient can then be assigned one of the likelihood ratios based on the pre-determined category that corresponds to the at least one secondary marker measurement corresponding to the patient.

The patient's likelihood ratio based on the BPD/OFD ratio and the patient's likelihood ratio based on the at least one secondary marker measurement can be used together or separately with other statistical processes to determine the patient's overall likelihood ratio. With respect to using these likelihood ratios together, such likelihood ratios, for example, can be multiplied together to determine the patient's overall likelihood ratio, particularly when the BPD/OFD ratio is statistically independent from the at least one secondary marker. If the BPD/OFD ratio is not statistically independent of the at least one secondary marker, the overall likelihood ratio can be determined by dividing the percentage of affected pregnancies by the percentage of unaffected pregnancies in each of the possible combinations of pre-determined categories for the BPD/OFD ratio and secondary marker.

In another implementation of this step of the method of the present invention, this implementation, the relative frequencies of each of the unaffected distribution and the affected distribution are determined by known statistical techniques. For example, the relative frequencies may be determined by a multivariate Gaussian distribution. In a multivariate Gaussian distribution, the relative frequency of each of the unaffected distribution and the affected distribution of each of the unaffected distribution and the affected distribution can be determined by the following formula:

$$\text{Relative Frequency} = \frac{\exp(-0.5 Z^T R^{-1} Z)}{(\prod(\sigma)(2 \times n)^{p/2} \det(R)^{1/2})}$$

where p=the number of secondary markers;
  $\Pi(\sigma)$=the product of the standard deviations for each marker;
  Z is vector containing the Z-score of each marker (the patient's marker value—the mean of the marker value from the affected or unaffected pregnancies)/the standard deviation of the marker value from the affected or unaffected pregnancies;

$Z^T$ is the transpose of Z;

R is a matrix of the reference data correlation coefficients between the BPD/OFD ratio marker and each secondary marker and between each pair of secondary markers; and det(R) is the determinant of the R matrix.

Parameters such as the standard deviation for the markers and the correlation coefficients are determined by known statistical techniques such as the maximum likelihood estimation for the parameter or by robust estimates which minimize the effect of outliers. Once the relative frequency for the affected distribution and the relative frequency of the unaffected distribution are determined by this multivariate analysis, the former can be divided by the latter to obtain the patient's likelihood ratio.

Since levels of many markers change through the course of gestation, the BPD/OFD ratios and the at least one secondary marker measurements may be normalized for gestational age prior to any comparisons. Such normalization may be performed by any method known in the art. For example, the values may be normalized by expressing the values as multiple of the median (MoM) values for unaffected pregnancies of the same gestational age (the same gestational age as the fetuses of the observed affected and observed unaffected pregnancies and the patient's fetus). Specifically, the MoM of the marker value can be obtained by dividing the value (such as the concentration or measurement) of the marker by the median value expected for that particular gestational age in women with unaffected pregnancies. Alternatively, the marker values may be normalized by using a delta method in which the expected mean of the marker values from unaffected pregnancies of the same gestational age are subtracted from the actual marker value from the patient or from the observed affected and the observed unaffected pregnancies. The markers may also be adjusted for by a known parameter, such as, for example, the crown-rump length, that varies with gestational age. The expected medians and means used in the MoM and delta methods can be derived from known statistical techniques such as linear or non-linear regression. With respect to BPD/OFD ratios of the patient's fetus and the fetal BPD/OFD ratios from the observed affected and the observed unaffected pregnancies, such normalization may not, however, be necessary.

In an implementation in which the BPD/OFD ratios and the at least one secondary marker measurements are normalized for gestational age using a delta method, the likelihood ratios are calculated by using expected gestational age-specific BPD/OFD ratios and/or expected gestational age-specific secondary marker measurements. For example, in this embodiment, each of the BPD/OFD ratios of the fetuses of the observed affected and the observed unaffected pregnancies are subjected to a linear regression equation to calculate an expected BPD/OFD ratio of each of the fetuses. For each of the observed affected and the observed unaffected pregnancies, a delta BPD/OFD ratio is calculated by subtracting the expected BPD/OFD ratio of the fetus from the actual observed BPD/OFD ratio of the fetus. The percentage of observed affected and observed unaffected pregnancies that belong to pre-determined categories of delta BPD/OFD ratios is then determined and the likelihood ratios for each pre-determined category is derived by dividing the percentage of observed affected pregnancies by the percentage of observed unaffected pregnancies for each pre-determined category. The patient's delta BPD/OFD ratio may be calculated by also subjecting the patient's fetus' BPD/OFD ratio to a linear regression equation to calculate the fetus' expected BPD/OFD ratio. The patient's fetus' delta BPD/OFD ratio is then calculated by subtracting the fetus' expected BPD/OFD ratio from the actual observed BPD/OFD ratio of the fetus. The patient may then be assigned one of the likelihood ratios based on the pre-determined category that corresponds to the delta BPD/OFD ratio of the patient's fetus. A similar approach can be used to determine the patient's likelihood ratio based on the at least one secondary marker measurement corresponding to the patient. The patient's likelihood ratio based on the delta BPD/OFD of the patient's fetus and the patient's likelihood ratio based on the delta at least one secondary marker measurement corresponding to the patient can be used together or separately with other statistical processes to determine the patient's overall likelihood ratio. With respect to using these likelihood ratios together, such likelihood ratios, for example, can be multiplied together to determine the patient's overall likelihood ratio of a fetal abnormality, particularly when the BPD/OFD ratio is statistically independent from the at least one secondary marker. If the BPD/OFD ratio is not statistically independent of the at least one secondary marker, the overall likelihood ratio can be determined by dividing the percentage of observed affected pregnancies by the percentage of observed unaffected pregnancies in each of the possible combinations of pre-determined categories for the delta BPD/OFD ratios and secondary marker measurements.

The patient's likelihood ratios based on the BPD/OFD ratio of the patient's fetus (or delta value thereof) and the at least one secondary marker measurement corresponding to the patient (or delta value thereof) can also be determined by other means known in the art. For example, there are numerous software packages that calculate likelihood ratios based on secondary screening marker measurements such as PAPP-A, free β hCG and/or nuchal translucency (many of which perform such calculations using a multivariate analysis).

As will be appreciated by one of skill in the art, any combination of the above-described approaches for deriving a likelihood ratio for the patient can be used in the present invention in the assessment of the patient's risk of a fetal abnormality. For example, the patient's likelihood ratio based on which pre-determined category of BPD/OFD ratios corresponds to the BPD/OFD ratio of the patient's fetus can be combined with the patient's likelihood ratio based on a multivariate statistical distribution analysis of the patient's at least one secondary screening marker measurement. Such a combination can include multiplying these two likelihood ratios together to determine the patient's overall likelihood ratio.

The next step of the present invention comprises using the patient's a priori risk of having a fetus with the fetal abnormality in conjunction with the comparison of the BPD/OFD ratio of the patient's fetus and the at least one secondary marker measurement corresponding to the patient to such values in observed affected and unaffected pregnancies. The patient's a priori risk of having a fetus with the fetal abnormality represents the incidence of fetal abnormality in other pregnant women with similar characteristics. For example, in Down Syndrome, the patient's a priori risk is determined based on maternal age, gestational age and/or whether the pregnant woman has had a previous pregnancy with Down Syndrome. Formulas to determine the a priori risk are known in the art and are described, for example, in Hecht C A, Hook E B. "The imprecision in rates of Down syndrome by one-year maternal age intervals. A critical analysis of rates used in biochemical screening," *Prenat*

Diagn; 14:729-38 (1994); Snidjers R J M, Sundberg K, Holzgreve W, Henry G, Nicolaides K. "Maternal age and gestation specific risk for trisomy 21," *Ultrasound Obstet Gynecol;* 13:167-70 (1993); Cuckle H. S., Wald N. J. and Thompson S G, "Estimating a woman's risk of having a pregnancy associated with Down's Syndrome using her age and serum alpha-fetoprotein level," *Br. J. OB/Gyn;* 94:387-392 (1987). The a priori risk based on maternal age can be adjusted for gestational age by multiplying the age related term-risk by the inverse (1–the fetal loss rate) at a given gestational age. For example, if the fetal loss rate was 30% and the a priori risk of Down syndrome was 1 in 1430 based on maternal age, then the gestational age adjusted risk would be 1/0.7/1430=1.43/1430=1 in 1000.

Once the patient's a priori risk has been determined, the a priori risk may be used with the comparison by multiplying the patient's likelihood ratio by the patient's a priori risk. The result of such a calculation provides the patient's risk of having a fetus with the fetal abnormality. As mentioned previously, even though all of the above methods of assessing the patient's risk of a fetal abnormality have been described with respect to a single secondary marker, it should be emphasized that any number of secondary markers can be used according to the present invention. For example, a plurality of likelihood ratios based on a plurality of secondary marker measurements can be derived and multiplied by the patient's a priori risk to determine the risk of fetal abnormality.

Furthermore, in any of the embodiments of the present invention, the BPD/OFD ratio of the patient's fetus and the fetal BPD/OFD ratios of the observed affected and the observed unaffected pregnancies can be expressed as the actual values of such markers or can be expressed as the logarithm or square root or other mathematical transformation of such markers prior to any comparisons. Similarly, the at least one secondary marker measurement corresponding to the patient and the at least one secondary marker measurements of the observed affected and the observed unaffected pregnancies can be expressed as the actual values of such markers or can be expressed as the logarithm, square root, or any other mathematical transformation of such markers prior to any comparisons. Moreover, the BPD/OFD ratios and the at least one secondary marker measurements may be adjusted for other factors known to affect marker values and measurements prior to any comparisons. Such factors include, for example, maternal weight, ethnic group, smoking status, insulin-dependency or other factors that may be associated with marker values or measurements.

Another aspect of the present invention provides a method of determining whether a patient is screen-positive or screen-negative for the fetal abnormality so that the patient, for example, can decide whether to undergo more testing, such as diagnostic testing. The method comprises selecting a risk cut-off level that will determine whether the patient is screen-positive or screen-negative. The method then includes determining a BPD/OFD ratio of the patient's fetus and at least one secondary marker measurement corresponding to the patient. A likelihood ratio of the patient is then calculated based on the BPD/OFD ratio of the patient's fetus and the at least one secondary marker measurement corresponding to the patient according to the methods described above, such as, for example, by multiplying the patient's likelihood ratio based on the BPD/OFD ratio of the patient's fetus by the patient's likelihood ratio based on the at least one secondary marker measurement corresponding to the patient. The patient's risk of a fetal abnormality is then calculated by multiplying the patient's likelihood ratio by the patient's a priori risk. The patient is then classified as screen-negative or screen-positive by comparing the patient's risk of the fetal abnormality to the risk cut-off level. Specifically, if the patient's risk is greater than or equal to the risk-cut off level, then the patient is screen-negative. The risk cut-off level can be determined based on the expected false positive rate if such a cut-off was used, based on the associated risk of follow-up testing, by a laboratory or clinician, on a case-by-case basis for each patient, or by any other criteria known to those of skill in the art. Such a classification of the patient as screen-positive or screen-negative for the fetal abnormality can help the clinician and patient make an informed decision as to whether the patient should undergo further diagnostic procedures.

In another aspect, the present invention provides a machine-readable medium having stored thereon a plurality of executable instructions, the plurality of executable instructions comprising receiving or calculating a BPD/OFD ratio of a patient's fetus and receiving at least one secondary marker measurement corresponding to the patient provided by a clinician, for example. The plurality of executable instructions further comprises performing a comparison of the BPD/OFD ratio of the patient's fetus and the at least one secondary marker measurement corresponding to the patient with observed relative frequency distributions of fetal BPD/OFD ratios and at least one secondary marker measurements from observed affected and observed unaffected pregnancies. The plurality of executable instructions further includes assessing the patient's risk of having a fetus with a fetal abnormality in view of a result of a comparison and the patient's a priori risk of having a fetus with the fetal abnormality.

Figure 2:
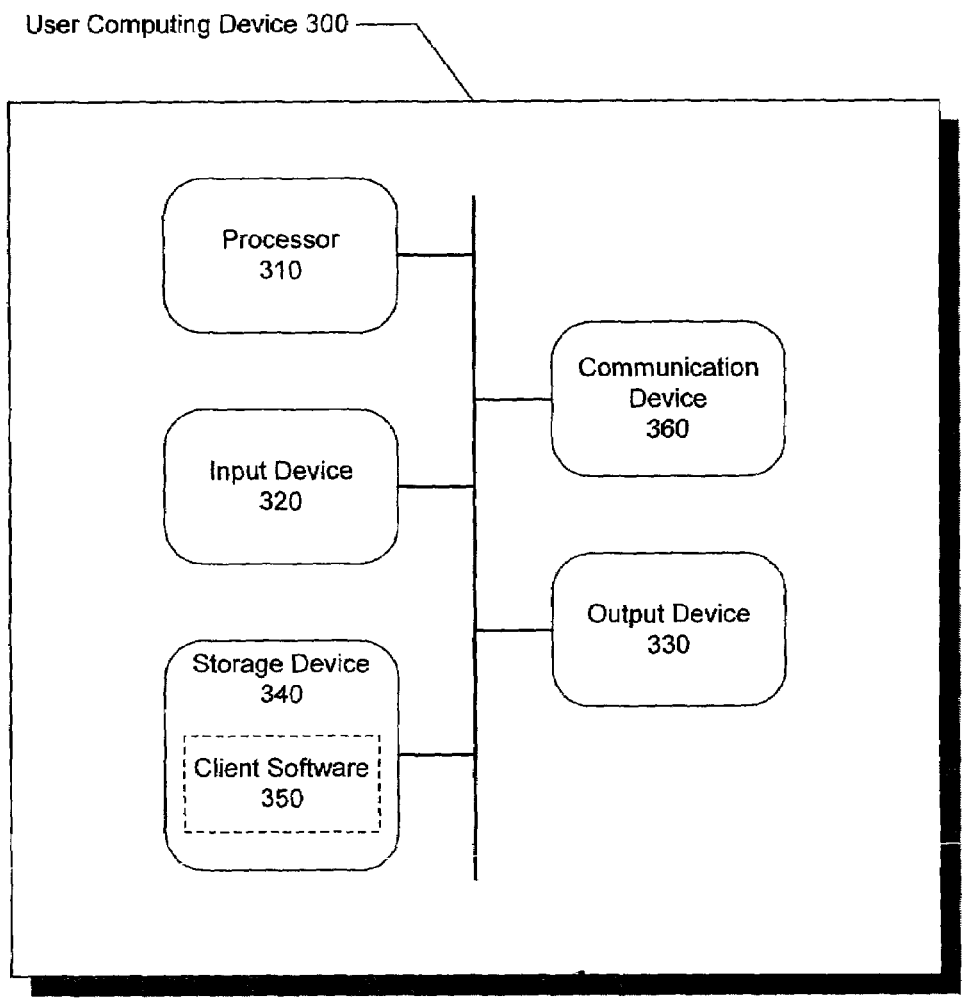
FIG. 2 is a block diagram that depicts an user computing device in accordance with an aspect of the present invention.
Figure 3:
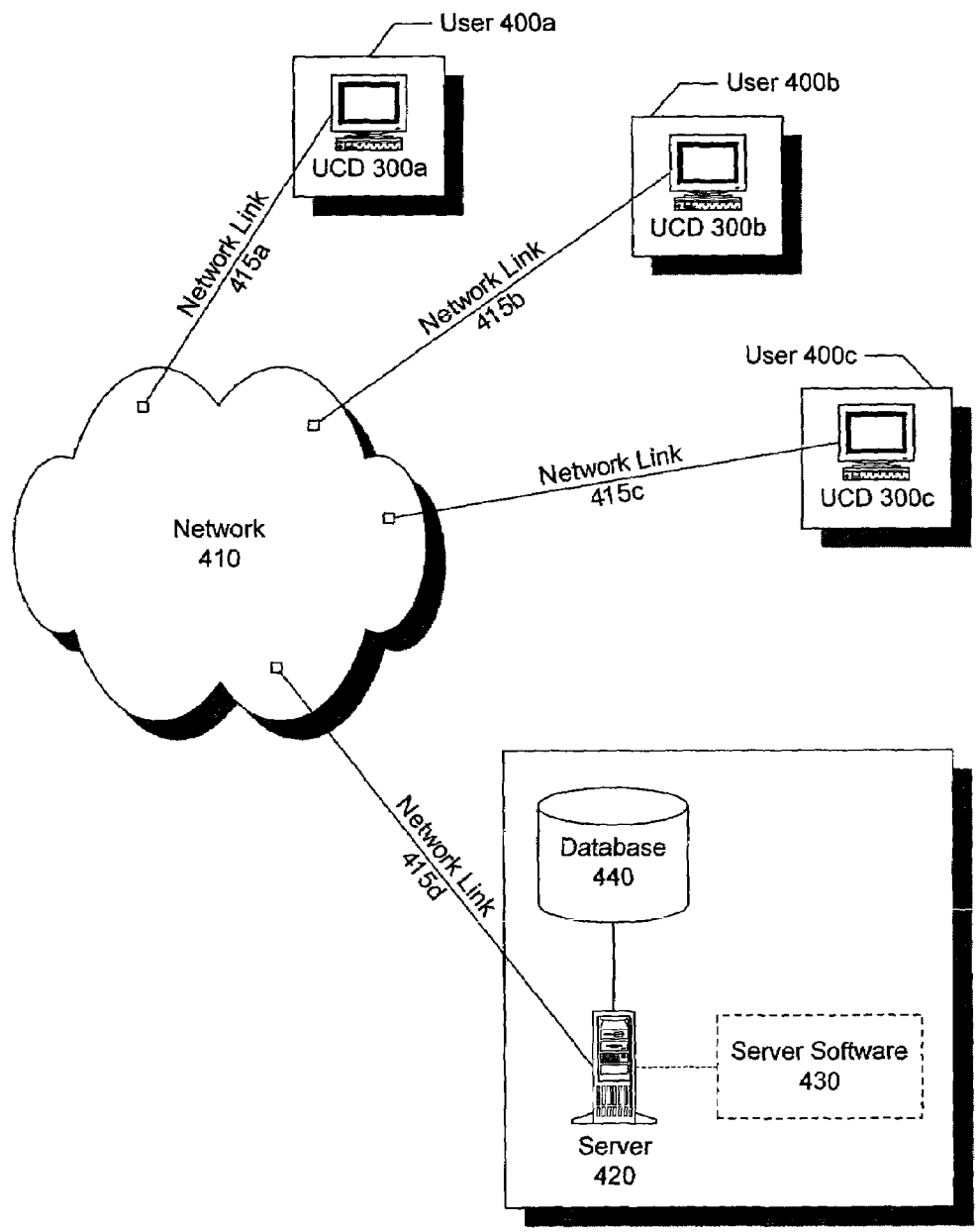
FIG. 3 is a block diagram that depicts a network architecture in accordance with an embodiment of the present invention.

Referring to FIG. 2, the machine-readable medium can be an user computing device 300 such as an ultrasound machine, MRI or CAT scan machine, fetoscopy machine, workstation, personal computer, handheld personal digital assistant ("PDA"), or any other type of microprocessor-based device. User computing device 300 may include a processor 310, input device 320, output device 330, storage device 340, client software 350, and communication device 360.

Input device 320 may include a keyboard, mouse, pen-operated touch screen, voice-recognition device, or any other device that accepts input. Output device 330 may include a monitor, printer, disk drive, speakers, or any other device that provides output.

Storage device 340 may include volatile and nonvolatile data storage, including one or more electrical, magnetic or optical memories such as a RAM, cache, hard drive, CD-ROM drive, tape drive or removable storage disk. Communication device 360 may include a modem, network interface card, or any other device capable of transmitting and receiving signals over a network. The components of user computing device 300 may be connected via an electrical bus or wirelessly.

Client software 350 may be stored in storage device 340 and executed by processor 310, and may include, for example, imaging and analysis software that embodies the functionality of the present invention.

Referring to FIG. 4, the analysis functionality of the present invention may be implemented on more than one user computing device 300 via a network architecture in accordance with an embodiment of the present invention. For example, in one embodiment, user computing device 300 may be an ultrasound machine that performs all of the BPD/OFD calculation functionality of the present invention. In another embodiment, user computing device 300a may be an ultrasound machine that performs the BPD/OFD calculation functionality of the present invention, and then transfers this calculation over network 410 to server 420 or user computing device 300b or 300c for analysis of the data with the at least one secondary marker measurement corresponding to the patient, for example. The analyzed data could further be transferred to another user computing device 300 belonging to the patient or another medical services provider for testing with others markers.

Network link 415 may include telephone lines, DSL, cable networks, T1 or T3 lines, wireless network connections, or any other arrangement that implements the transmission and reception of network signals. Network 410 may include any type of interconnected communication system, and may implement any communications protocol, which may secured by any security protocol.

Server 420 includes a processor and memory for executing program instructions, as well as a network interface, and may include a collection of servers. In one particular embodiment, server 420 may include a combination of servers such as an application server and a database server. Database 440 may represent a relational or object database, and may be accessed via server 420.

User computing device 300 and server 420 may implement any operating system, such as Windows or UNIX. Client software 350 and server software 430 may be written in any programming language, such as ABAP, C, C++, Java or Visual Basic.

EXAMPLES

Example 1

The present example illustrates calculating likelihood ratios for pre-determined categories of BPD/OFD ratios using fetal BPD/OFD ratios from reference data of observed affected and observed unaffected pregnancies.

520 unaffected pregnancies and 15 Down Syndrome pregnancies were analyzed and the pregnancies were categorized into pre-determined categories of BPD/OFD ratios. In particular, for each pre-determined category, the number of unaffected pregnancies, the number of affected pregnancies, the relative frequency of affected distribution, the relative frequency of unaffected distribution, and the likelihood ratios were calculated as shown in Table II.

the relative frequency of the affected distribution by the relative frequency of the unaffected distribution for each of the predetermined categories.

To assess the BPD/OFD ratio as a marker in a multiple marker screening protocol, a reference data set of 4953 unaffected pregnancies and 29 Down Syndrome pregnancies between 11 weeks, 1 day gestational age and 13 weeks, 6 days gestational age from a previous study on nuchal translucency, free-β hCG and PAPP-A was analyzed (described in more detail in Krantz et al., "First Trimester Down Syndrome Using Dried Blood Biochemistry and Nuchal Translucency," *Obstet. Gynecol.*, Vol. 96, pp. 207-211 (2000)). A random number generator was used to assign each pregnant woman in the dataset to one of the four pre-determined categories indicated in Table II. A new likelihood ratio based on the combination of fetal BPD/OFD ratios, nuchal translucency measurements, free β-hCG levels, and PAPP-A levels was calculated by multiplying the likelihood ratio determined from the random generator with the likelihood ratio previously determined based on nuchal translucency, free β-hCG, and PAPP-A.

The modified likelihood ratios were then modeled using the maternal age distribution of live births in the United States to determine the false positive rate and the detection rate. False positive and detection rates were modeled using observed likelihood ratios and the maternal age distribution of live births. For each maternal age 14-49, age-specific false positive and detection rates were determined based on the observed likelihood ratios, the a priori risk at that maternal age and a cut-off risk. The overall false positive rate was then determined by taking a weighted average of the age-specific false positive rates, where the weights were equal to the number of unaffected pregnancies in the United States at each maternal age divided by the total number of unaffected pregnancies in the United States. Similarly, the overall detection rate was determined by taking a weighted average of the age-specific detection rates, where the weights were equal to the number of Down Syndrome pregnancies at each maternal age divided by the total number of Down Syndrome pregnancies. The number of Down syndrome pregnancies was estimated by multiplying the number of live births at each maternal age by the incidence rate of Down syndrome. To determine the false positive rate at an 85% detection rate the cut-off risk was

TABLE II

| BPD/OFD ratio Category | Number of Unaffected Pregnancies | Number of Affected Pregnancies | Relative Frequency of Unaffected Distribution | Relative Frequency of Affected Distribution | Likelihood Ratio |
|---|---|---|---|---|---|
| <0.8261 | 261 | 3 | 50.2% | 20.0% | .3985 |
| 0.8262-0.8781 | 207 | 5 | 39.8% | 33.3% | .8374 |
| 0.8782-0.8930 | 26 | 1 | 5% | 6.67% | 1.333 |
| >0.8930 | 26 | 6 | 5% | 40.0% | 8.000 |
| Total | 520 | 15 | — | — | — |

For each pre-determined category, the relative frequency of the unaffected distribution was the percentage of unaffected pregnancies in each category. Similarly, for each pre-determined category, the relative frequency of the affected distribution was the percentage of the affected pregnancies in each category. Likelihood ratios were developed for each of the pre-determined categories by dividing varied until the cut-off risk at which an 85% detection rate was observed and then determining the false positive rate at that cut-off.

The model procedure was repeated 100 times and the median false positive rate and detection rate were determined. Using this procedure, a false positive rate of 3.0% and a detection rate of 90% were achieved.

Example 2

The present example discloses calculating delta values for fetal BPD/OFD ratios in reference data of observed affected and observed unaffected pregnancies and deriving likelihood ratios based on Gaussian distributions.

520 unaffected and 15 Down syndrome pregnancies were analyzed. The natural log of the fetal BPD/OFD ratios were regressed against the natural log of the crown rump length (CRL) using linear regression and the following equation obtained:

Expected $BPD/OFD$ ratio marker value=EXP($-0.2947+0.0251 \times ln(CRL)$)

A "delta value" was then calculated for each fetus of the unaffected and the Down syndrome pregnancies by subtracting the fetus' expected BPD/OFD ratio from the fetus' actual observed BPD/OFD ratio.

The observed mean and standard deviation delta BPD/OFD ratios of the unaffected pregnancies were 0.0 and 0.03637. The observed mean and standard deviation delta BPD/OFD ratios of the affected pregnancies were 0.0428 and 0.04422.

A correlation analysis of the delta BPD/OFD ratios and natural log nuchal translucency MoM values from the same pregnancies was conducted. The correlation of delta BPD/OFD ratios and delta nuchal translucency was 0.1399 in unaffected pregnancies and −0.0042 in affected pregnancies.

Gaussian distributions were then developed using these parameters and previously published parameters for nuchal translucency (NT) MoM values, free β-hCG MoM values and PAPP-A MoM values, as indicated in Table III.

TABLE III

| | Unaffected Pregnancies | Affected Pregnancies |
|---|---|---|
| Mean | | |
| Delta BPD/OFD ratio[1] | 0.0 | .0428 |
| NT MoM[2] | 0.0 | .7023 |
| Free β-hCG MoM[3] | 0.0 | .6831 |
| PAPP-A MoM[3] | 0.0 | −.4308 |
| Standard Deviation | | |
| Delta BPD/OFD ratio[1] | .03637 | .04422 |
| NT MoM[2] | .2763 | .5411 |
| Free β-hCG MoM[3] | .5561 | .3454 |
| PAPP-A MoM[3] | .5330 | .5476 |
| Correlations | | |
| Delta BPD/OFD ratio | | |
| Vs. NT MoM[1] | .1399 | −.0042 |
| Vs. free β-hCG MoM[4] | 0.0 | 0.0 |
| Vs. PAPP-A MoM[4] | 0.0 | 0.0 |
| NT MoM | | |
| Vs. free β-hCG MoM[4] | 0.0 | 0.0 |
| Vs. PAPP-A MoM[4] | 0.0 | 0.0 |
| Free β-hCG MoM | | |
| Vs. PAPP-A MoM[3] | .194 | .217 |

[1]Observed in 520 unaffected and 15 Down Syndrome pregnancies.
[2]Published data from Nicolaides KH, Snijders RJM, Cuckle HS, "Correct estimation of parameters for ultrasound nuchal translucency screening." Prenat Diagn 18: 511-523 (1998). The data was converted from log10 (MoM) to ln(MoM).
[3]Published data from Krantz DA, Hallahan TW, Orlandi F, Buchanan P, Larsen JW, Macri JN, "First-Trimester Down syndrome screening using dried blood biochemistry and nuchal translucency." Obstet Gynecol 96: 207-213 (2000).
[4]Correlation between ultrasound markers and biochemistry markers was set equal to zero.

To assess the multi-marker screening protocol involving the screening markers of BPD/OFD ratio, nuchal translucency, free β-hCG, and PAPP-A, a simulation trial was conducted in which sets of delta BPD/OFD ratio values, nuchal translucency MoM, free β-hCG MoM and PAPP-A MoM values were generated for 100,000 simulated unaffected pregnancies using the above unaffected parameters and for 100,000 simulated Down Syndrome pregnancies using the above affected parameters. False positive and detection rates were modeled using simulated likelihood ratios and the maternal age distribution of live births. For each maternal age 14-49, age-specific false positive and detection rates were determined based on the simulated likelihood ratios, the a priori risk at that maternal age and a cut-off risk. The overall false positive rate was then determined by taking a weighted average of the age-specific false positive rates, where the weights were equal to the number of unaffected pregnancies in the United States at each maternal age divided by the total number of unaffected pregnancies in the United States. Similarly, the overall detection rate was determined by taking a weighted average of the age-specific detection rates, where the weights were equal to the number of Down syndrome pregnancies at each maternal age divided by the total number of Down syndrome pregnancies. The number of Down syndrome pregnancies was estimated by multiplying the number of live births at each maternal age by the incidence rate of Down syndrome. To determine the false positive rate at an 85% detection rate the cut-off risk was varied until the cut-off risk at which an 85% detection rate was observed and then determining the false positive rate at that cut-off.

Using the age distribution of live births in the United States, at a fixed 85% detection rate, the false positive rate with nuchal translucency, free β-hCG and PAPP-A was 3.8%. Including the BPD/OFD ratio reduce the false positive rate to 2.3%, a 40% reduction.

The foregoing description and examples have been set forth merely to illustrate the invention and are not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

We claim:

1. A method of assessing a patient's risk of having a fetus with a fetal abnormality comprising:
   determining the patient's a priori risk of having a fetus with the fetal abnormality;
   determining a bi-parietal diameter to occipito-frontal diameter (BPD/OFD) ratio of a patient's fetus during the first trimester of pregnancy;
   determining an at least one secondary marker measurement corresponding to the patient during a first trimester of pregnancy;
   performing a comparison of the BPD/OFD ratio of the patient's fetus and the at least one secondary marker measurement corresponding to the patient with observed relative frequency distributions of fetal BPD/

OFD ratios and at least one secondary marker measurements from observed affected and observed unaffected pregnancies; and assessing the patient's risk of having a fetus with a fetal abnormality in view of a result of the comparison and the patient's a priori risk of having a fetus with the fetal abnormality, wherein the fetal abnormality is a craniofacial abnormality, a chromosomal abnormality, or a developmental central nervous system abnormality.

2. The method of claim 1, wherein the fetal abnormality is a chromosomal abnormality.

3. The method of claim 2, wherein the chromosomal abnormality is a trisomic abnormality.

4. The method of claim 3, wherein the trisomic abnormality is Down Syndrome, trisomy 13, or trisomy 18.

5. The method of claim 4, wherein the trisomic disorder is Down's Syndrome.

6. The method of claim 1, wherein the fetal abnormality is open spina bifida.

7. The method of claim 1, wherein determining the at least one secondary marker measurement corresponding to the patient comprises measuring or obtaining measurements of a biochemical marker from the fetus or the patient.

8. The method of claim 7, wherein the biochemical marker is selected from a group consisting of total human chorionic gonadotropin, alpha fetoprotein, unconjugated estriol, total estriol, pregnancy associated placental protein A, inhibin A, free beta hCG, free alpha hCG, and hyperglycosylated hCG.

9. The method of claim 1, wherein determining the at least one secondary marker measurement corresponding to the patient comprises measuring or obtaining measurements of an ultrasound marker from the fetus.

10. The method of claim 9, wherein the ultrasound marker is selected from a group consisting of nuchal translucency, nuchal fold thickness, femur length, humerus length, hyperechogenic bowel, renal pyelectasis, fetal heart rate, echogenic foci, ductus venosus blood flow, absent or hypoplastic nasal bone, intra-uterine growth retardation, exomphalos, and micrognathia.

11. The method of claim 1, wherein the at least one secondary marker measurement corresponding to the patient and the at least one secondary marker measurements from the observed affected and the observed unaffected pregnancies are each a plurality of secondary marker measurements.

12. The method of claim 1, wherein performing the comparison comprises: grouping the fetal BPD/OFD ratios from the observed affected and the observed unaffected pregnancies into pre-determined categories of BPD/OFD ratios; deriving likelihood ratios for each of the pre-determined categories; and assigning the patient one of the likelihood ratios based on the one of the pre-determined categories that corresponds to the BPD/OFD ratio of the patient's fetus.

13. The method of claim 1, wherein performing the comparison comprises: grouping the at least one secondary marker measurements from the observed affected and the observed unaffected pregnancies into pre-determined categories of secondary marker measurements; deriving likelihood ratios for each of the pre-determined categories; and assigning the patient one of the likelihood ratios based on the one of the predetermined categories that corresponds to the at least one secondary marker measurement corresponding to the patient.

14. The method of claim 1, wherein performing the comparison comprises:
grouping the fetal BPD/OFD ratios from the observed affected and the observed unaffected pregnancies into pre-determined category of fetal BPD/OFD ratios;
deriving a first set of likelihood ratios for each of the pre-determined category of fetal BPD/OFD ratios;
assigning to the patient a first likelihood ratio from the first set of likelihood ratios based on the one of the pre-determined categories of fetal BPD/OFD ratios that corresponds to the BPD/OFD ratio of the patient's fetus;
grouping the at least one secondary marker measurements from the observed affected and the observed unaffected pregnancies into pre-determined categories of secondary marker measurements;
deriving a second set of likelihood ratios for each of the pre-determined categories of secondary marker measurements;
assigning to the patient a second likelihood ratio from the second set of likelihood ratios based on the one of the pre-determined categories of secondary marker measurements that corresponds to the at least one secondary marker measurement corresponding to the patient; and
multiplying the patient's first likelihood ratio by the second likelihood ratio to obtain an overall likelihood ratio.

15. The method of claim 1, wherein performing the comparison comprises deriving a likelihood ratio for the patient using a multivariate statistical analysis.

16. The method of claim 15, wherein the multivariate statistical analysis comprises a multivariate Gaussian analysis.

17. The method of claim 1, further comprising normalizing the at least one secondary marker measurement corresponding to the patient and the at least one secondary marker measurements from the observed affected and the observed unaffected pregnancies for gestational age prior to performing the comparison.

18. The method of claim 17, wherein normalizing comprises expressing the at least one secondary marker measurement corresponding to the patient and the at least one secondary marker measurements from the observed affected and the observed unaffected pregnancies as a multiple of the median measurement in unaffected pregnancies of the same gestational age.

19. The method of claim 1, wherein determining the BPD/OFD ratio of the patient's fetus comprises calculating a delta value thereof and performing the comparison comprises comparing the delta value of the BPD/OFD ratio of the patient's fetus to delta values of fetal BPD/OFD ratios from the observed affected and the observed unaffected pregnancies.

20. The method of claim 1, wherein determining the at least one secondary marker measurement corresponding to the patient comprises calculating a delta value thereof and performing the comparison comprises comparing the delta value of the patient's at least one secondary marker measurement to delta values of the at least one secondary marker measurements from the observed affected and the observed unaffected pregnancies.

21. The method of claim 1, wherein performing the comparison comprises: determining a first delta value of the BPD/OFD ratio of the patient's fetus; deriving a first set of likelihood ratios for pre-determined categories of delta values of BPD/OFD ratios; assigning to the patient a first likelihood ratio from the first set of likelihood ratios based on the one of the pre-determined categories of delta values of BPD/OFD ratios that corresponds to the patient's first delta value; determining a second delta value of the at least one secondary marker measurement corresponding to the patient; deriving a second set of likelihood ratios for pre-determined categories of delta values of secondary marker measurements; assigning to the patient a second likelihood ratio from the second set of likelihood ratios based on the one of the pre-determined categories of delta values of secondary marker measurements that corresponds to the patient's second delta value; multiplying the first likelihood ratio by the second likelihood ratio to obtain an overall likelihood ratio.

22. The method of claim 1, wherein performing the comparison comprises comparing a mathematical transformation of the BPD/OFD ratio of the patient's fetus to a mathematical transformation of the fetal BPD/OFD ratios from the observed affected and the observed unaffected pregnancies.

23. The method of claim 22, wherein the mathematical transformation of the BPD/OFD ratio of the patient's fetus and the mathematical transformation of the fetal BPD/OFD ratios from the observed affected and the observed unaffected pregnancies each comprises a logarithm.

24. The method of claim 22, wherein the mathematical transformation of the BPD/OFD ratio of the patient's fetus and the mathematical transformation of the fetal BPD/OFD ratios from the observed affected and the observed unaffected pregnancies each comprises a square root.

25. The method of claim 1, wherein performing the comparison comprises comparing a mathematical transformation of the at least one secondary marker measurement corresponding to the patient to a mathematical transformation of the at least one secondary marker measurements from the observed affected and the observed unaffected pregnancies.

26. The method of claim 25, wherein the mathematical transformation of the at least one secondary marker corresponding to the patient and the at least one secondary marker from the observed affected and the observed unaffected pregnancies each comprises a logarithm.

27. The method of claim 25, wherein the mathematical transformation of the at least one secondary marker corresponding to the patient and the at least one secondary marker from the observed affected and the observed unaffected pregnancies each comprises a square root.

28. The method of claim 1, wherein the chromosomal abnormality is triploidy.

29. A method of assessing a patient's risk of having a fetus with a fetal abnormality comprising:
   determining the patient's a priori risk of having a fetus with the fetal abnormality;
   determining a bi-parietal diameter to occipito-frontal diameter (BPD/OFD) ratio of a patient's fetus comprising measuring or obtaining measurements of an occipito-frontal diameter and a bi-parietal diameter of the patient's fetus during a first trimester of pregnancy;
   determining an at least one secondary marker measurement corresponding to the patient during the first trimester of pregnancy;
   performing a comparison of the BPD/OFD ratio of the patient's fetus and the at least one secondary marker measurement corresponding to the patient with observed relative frequency distributions of fetal BPD/OFD ratios and at least one secondary marker measurements from observed affected and observed unaffected pregnancies; and
   assessing the patient's risk of having a fetus with a fetal abnormality in view of a result of the comparison and the patient's a priori risk of having a fetus with the fetal abnormality, wherein the fetal abnormality is a chromosomal abnormality, a craniofacial abnormality, or a developmental central nervous system abnormality.

30. The method of claim 29, wherein the fetal abnormality is a chromosomal abnormality.

31. The method of claim 30, wherein the chromosomal abnormality is triploidy.

32. The method of claim 30, wherein the chromosomal abnormality is a trisomic abnormality.

33. The method of claim 32, wherein the trisomic abnormality is Down Syndrome, trisomy 13, or trisomy 18.

34. The method of claim 33, wherein the trisomic abnormality is Down Syndrome.

35. The method of claim 29, wherein the fetal abnormality is open spina bifida.

36. A method of assessing whether a patient is screen-positive or screen-negative for having a fetus with a fetal abnormality, the method comprising:
   selecting a risk cut-off level for determining whether a patient is screen-positive or screen-negative for having a fetus with a fetal abnormality;
   determining a BPD/OFD ratio of the patient's fetus during the first trimester of pregnancy and at least one secondary marker measurement corresponding to the patient;
   calculating a likelihood ratio of the patient based on the BPD/OFD ratio of the patient's fetus and the at least one secondary marker measurement corresponding to the patient; multiplying the patient's likelihood ratio by the patient's a priori risk to determine the patient's risk of a fetal abnormality; and
   assessing whether the patient is screen-positive or screen-negative by comparing the patient's risk of a fetal abnormality to the risk-cut off level, wherein if the patient's risk is greater than or equal to the risk-cut off level, then the patient is screen-positive and if the patient's risk is less than the riskcut-off level, then the patient is screen-negative.

37. A method of assessing a patient's risk of having a fetus with a fetal abnormality, the method comprising: determining an OFD/BPD ratio of a patient's fetus; determining at least one secondary marker measurement corresponding to the patient;
   performing a comparison of the OFD/BPD ratio of the patient's fetus and the at least one secondary marker measurement corresponding to the patient with observed relative frequency distributions of fetal OFD/BPD ratios during the first trimester of pregnancy and at least one secondary marker measurements from observed affected and observed unaffected pregnancies; and
   assessing the patient's risk of having a fetus with a fetal abnormality in view of a result of the comparison and the patient's a priori risk of having a fetus with the fetal abnormality.

38. A machine-readable medium having stored thereon a plurality of executable instructions, the plurality of executable instructions comprising:

receiving or calculating a BPD/OFD ratio of a patient's fetus during a first trimester of pregnancy;

receiving at least one secondary marker measurement corresponding to the patient during a first trimester of pregnancy;

performing a comparison of the BPD/OFD ratio of the patient's fetus and the at least one secondary marker measurement corresponding to the patient with observed relative frequency distributions of fetal BPD/OFD ratios and at least one secondary marker measurements from observed affected and observed unaffected pregnancies;

assessing the patient's risk of having a fetus with a fetal abnormality in view of a result of the comparison and the patient's a priori risk of having a fetus with the fetal abnormality and outputting risk results to a user.

* * * * *